United States Patent [19]

Kuzmick et al.

[11] Patent Number: 4,468,217
[45] Date of Patent: Aug. 28, 1984

[54] SURGICAL SUCTION TIP WITH FILTER

[76] Inventors: Kenneth M. Kuzmick, 2596 Old Military Trail, West Palm Beach, Fla. 33409; William E. Anspach, Jr., 12158 Edgewater Dr., Lake Park, Fla. 33403

[21] Appl. No.: 396,945

[22] Filed: Jul. 9, 1982

[51] Int. Cl.³ ............................................ A61M 31/00
[52] U.S. Cl. ...................................... 604/48; 604/902; 604/319; 433/92
[58] Field of Search .................. 285/361, 402; 55/467, 55/470, 471, 502; 433/92, 133, 114, 126; 604/902, 49–54, 65, 66, 73, 75, 76, 93, 111, 48, 118, 119, 128, 129, 173, 190, 276, 290, 319; 15/347, 350

[56] References Cited
U.S. PATENT DOCUMENTS

| | | | |
|---|---|---|---|
| 2,047,714 | 7/1936 | Smith, Sr. | 285/402 |
| 3,676,986 | 7/1972 | Reiling | 55/472 |
| 3,785,380 | 1/1974 | Brumfield | 604/902 |

Primary Examiner—John D. Yasko
Assistant Examiner—J. L. Kruter
Attorney, Agent, or Firm—Jack N. McCarthy

[57] ABSTRACT

A surgical suction tip includes an outer housing and an inner removable filter device. The housing includes a suction opening at one end and a filter receiving handle formed as a sleeve at the other end; the inner removable filter device is connected in the filter receiving handle by a quick connect-disconnect means; the housing tapers so as to increase in size from its suction opening to the filter device. A seal is located between the housing and filter device.

6 Claims, 4 Drawing Figures

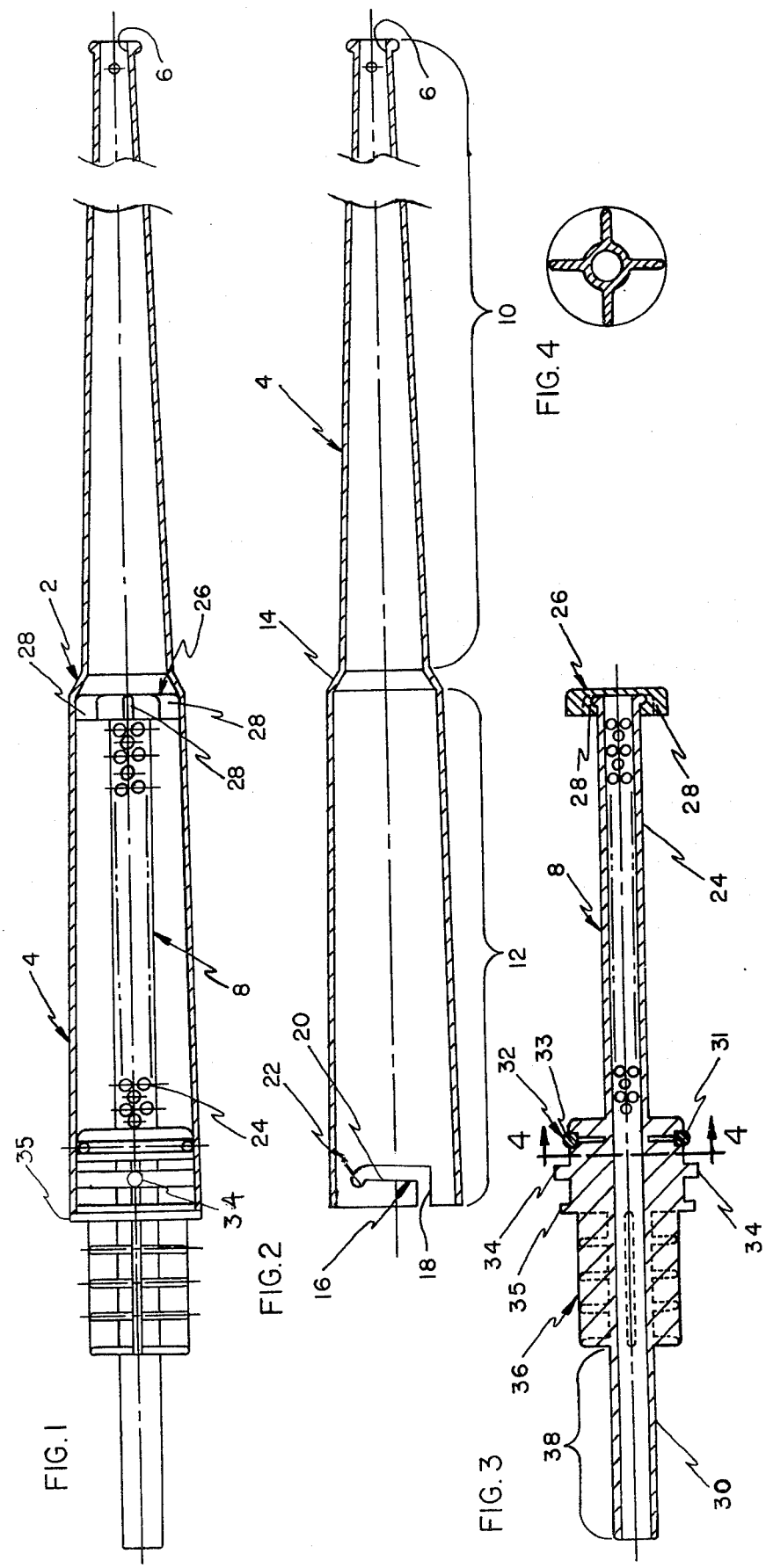

SURGICAL SUCTION TIP WITH FILTER

TECHNICAL FIELD

This invention relates to the field of surgical instruments and more particularly to a surgical suction tip with a filter in the handle for removing fluid from the body, including liquid blood and serum, while collecting large blood clots, fragments of bone, tissue, and other solid waste.

BACKGROUND ART

Aspirator devices are commonly used in surgical procedures for a wide variety of applications. It is typical to provide a suction device with one or more openings immediately at the tip for aspirating, or sucking, fluids. However, these devices have been easily clogged by bits of tissue and other matter. Some devices provide a suction source combined with a sponge or other filter, such as a screen, at their tip. Further, some aspirating tips at the end of a suction hose have variable area nozzles to control the size of the suction orifice.

Some known prior art patents for these suction and aspirating devices are herein set forth: U.S. Pat. Nos. 3,520,300; 4,068,644; 3,169,528; 3,918,453; 4,036,232; and 4,204,328.

DISCLOSURE OF INVENTION

It is an object of this invention to provide a surgical suction tip having a filter which can be immediately removed by the surgeon upon a blocked condition, cleaned, and replaced in a minimum amount of time—a few seconds.

Another object of this invention is to provide a surgical suction tip formed of two main parts, an outer contoured housing having a suction opening at one end and an inner removable filter device being held in position in said outer housing at its other end by a quick attach-detach (connect-disconnect) coupling device.

A further object of this invention is to form the outer housing enclosing the inner removable filter device with a material, such as a plastic, which is clear so that the surgeon can tell when the filter is becoming full.

Another object of this invention is that the end of the outer housing containing the removable inner filter forms the handle for the surgical suction tip.

BRIEF DESCRIPTION OF THE DRAWINGS

FIG. 1 is a view of the surgical suction tip having the outer contoured housing in section with the inner removable filter device in its assembled position;

FIG. 2 is a longitudinal sectional view of the outer contoured housing;

FIG. 3 is a longitudinal sectional view of the inner removable filter device with the forward end cap and guiding device in place; and FIG. 4 is a view taken along the line 4—4 of FIG. 3.

BEST MODE FOR CARRYING OUT THE INVENTION

A surgical suction tip (FIG. 1) is formed of two main parts: (1) an outer contoured housing 4 having a suction opening 6 at one end thereof; and (2) an inner removable filter device 8.

The outer contoured housing 4 is formed having an elongated suction tube section 10 slightly tapered outwardly from its opening 6 with a filter receiving handle sleeve section 12 also being slightly tapered outwardly from where it is attached to the suction tube section 10 by a conical section 14 which is tapered outwardly in the same direction as the other two sections, but having a larger taper angle. Two contoured notches 16 are formed in diametrically opposed sides of the large open end of the filter receiving handle sleeve section 12. Each notch 16 is formed having a short notch section 18 extending inwardly from the unattached end of the sleeve section 12, a longer circumferential notch section 20 extending therefrom around the circumference of the sleeve 12 (for approximately one-fourth of the circumference), and a very short pin retaining notch section 22 extending therefrom toward the unattached end of the sleeve section 12. Each longer circumferential notch section 20 tapers slightly away from the unattached end of the sleeve section 12 as it extends around the circumference of the sleeve section 12 towards the very short notch section 22 for a purpose to be hereinafter described.

The inner removable filter device 8 is formed having approximately one-half of its length formed as a cylindrical filter 24, while the remaining one-half of its length is formed as a tubular member 30 extending from said cylindrical filter 24 having an enlarged portion thereon. The cylindrical filter 24 is sized to fit within the filter receiving handle sleeve section 12 providing an annular space therebetween and is formed having openings therethrough to pass fluids while collecting large clots, fragments of bone, tissue and other solid waste. The free open end of the cylindrical filter 24 is formed having a cap member 26 fixed thereon, by being snapped over a bead on the end, to close the end of the cylindrical filter 24 and provide four equally-spaced guide flanges 28 for guiding and positioning the free end of the cylindrical filter 24 within the filter receiving sleeve section 12 and spaces therebetween for permitting flow from said elongated suction tube section 10 into said annular space between filter receiving section 12 and said cylindrical filter 24.

The enlarged portion of tubular member 30 of filter device 8 provides a seal means 32 which provides a seal with the interior of the filter receiving sleeve section 12; provides a pair of radially projecting pins 34 and end flange 35; pins 34 cooperate with the contoured notches 16 in a manner to be hereinafter described and end flange 35 contacts the end of the sleeve section 12; and provides crossed flange means 36 for grasping the inner removable filter device 8 to rotate it relative to said filter receiving handle sleeve section 12 to remove the filter device 8 and reinsert it. A short tubular end 38 of tubular member 30 is provided with a slight taper to receive one end of a conventional suction tube. While the conventional suction tube can be merely pressed over the short tubular end 38, other connecting means can be provided to hold the suction tube to the filter device 8. The seal means 32 comprises an O-ring groove 31 and O-ring 33 and the crossed flange means 36 for grasping the inner removable filter device 8 comprises four longitudinal flanges and four intersecting circumferential flanges.

To connect the inner removable filter device 8 to the outer contoured housing 4, the crossed flange means 36 is held in one hand, while the filter receiving handle sleeve section 12 is held in the other hand, the cap member 26 with the four equally-spaced guide flanges 28 is inserted into the open end of the filter receiving handle sleeve section 12. The inner removable filter device 8 is moved inwardly until the pins 34 are each aligned with its cooperating short notch section 18; each pin 34 moves along its short notch section 18 until it reaches the longer circumferential notch section 20. At this time, the end flange 35 contacts the end of the sleeve section 12. The filter device 8 and housing 4 are then relatively rotated so that each notch moves along its cooperating notch section 20 which tapers away from the end of the sleeve section 12. This places a slight force between the pin 34 and its cooperating notch section 20 so that when it reaches the end of its notch section 20, it snaps into the short pin retaining notch section 22 where it holds the outer contoured housing 4 to the inner removable filter device 8. While one specific quick attach-detach coupling device has been described, other such coupling devices can be used.

To disconnect the inner removable filter device 8 from the outer contoured housing 4, the crossed flange means 36 is held in one hand, while the filter receiving handle sleeve section 12 is held in the other hand and with a slight force pressing the removable filter device 8 into the outer contoured housing 4, the members are rotated in relation to each other so that the pins 34 are moved out of their pin retaining notch sections 22 and moved along the notch sections 20 and notch sections 18, thereby permitting the filter device 8 and outer contoured housing 4 to be separated whereby any filtered material can then be removed and the units reconnected as set forth above.

We claim:

1. A suction tip for removing fluid and solid material from a body cavity during a surgical operation comprising an elongated housing, said elongated housing being formed by a first and second hollow elongated tapered section means connected together by a short hollow conical section means, said housing including a suction opening at the end of said second hollow elongated tapered section means and said first hollow elongated tapered section means forming a filter receiving handle sleeve means at the other end, said filter receiving handle sleeve means having an inner surface and an open end, an inner removable filter means being positioned within the inner surface of said filter receiving handle sleeve means, said inner removable filter means having a cylindrical filter with guide means on its end within said inner surface of said filter receiving handle sleeve means, said guide means comprising equally spaced guide flanges extending radially outwardly from said cylindrical filter towards the inner surface of said filter receiving handle sleeve means adjacent said short hollow conical section means, said guide flanges guiding the end of said cylindrical filter and positioning it within said filter receiving handle sleeve means, means sealing said inner removable filter means with the inner surface of said filter receiving handle sleeve means, quick connect-disconnect means connecting said inner removable filter means to said filter receiving handle sleeve means, said inner removable filter means having a tubular portion extending through said open end of said filter receiving handle sleeve means externally of said filter receiving handle sleeve means to direct fluid and filtered solid material therefrom.

2. A suction tip as set forth in claim 1 wherein the elongated housing tapers so as to increase in size from its suction opening to the filter receiving handle sleeve means.

3. A suction tip as set forth in claim 1 wherein said inner removable filter means has a tubular filter section projecting into said filter receiving handle sleeve means, said tubular filter section having means for guiding it and positioning it centrally within said filter receiving handle sleeve means, said means sealing said inner removable filter means with the inner surface of said filter receiving handle sleeve means including an O-ring seal adjacent the tubular filter section.

4. A combination as set forth in claim 3 wherein said inner removable filter means has an annular flange thereon, said filter receiving handle sleeve means having an end surface at its open end which engages said annular flange when said inner removable filter means is inserted thereinto, said end surface of said filter receiving handle sleeve means being held against the annular flange by said quick connect-disconnect means.

5. A suction tip for removing fluid and solid material from a body cavity during a surgical operation comprising an elongated housing, said housing including a first elongated hollow suction tube section having a suction opening at one end and a second elongated hollow filter receiving handle sleeve means connected thereto at the other end by a short hollow conical section means, said second elongated hollow filter receiving handle sleeve means having an inner surface and an open end, said first elongated hollow suction tube section tapering so as to increase in size from its suction opening to the short hollow conical section means, said second elongated hollow filter receiving handle sleeve means tapering so as to increase in size from said short hollow conical section means to its open end, an inner removable filter means extending into said second elongated hollow filter receiving handle sleeve means through said open end, said inner removable filter means having a tubular filter section with a free end positioned in said second elongated hollow filter receiving handle sleeve means, said housing being formed of a clear plastic so that one can see the tubular filter section, said tubular filter section having equally spaced flange means on its free end for guiding it and positioning it centrally within said second elongated hollow filter receiving handle sleeve means adjacent said short hollow conical section means, said flange means extending radially outwardly from said tubular filter section towards the inner surface of said second elongated hollow filter receiving handle sleeve means, said inner removable filter means having an enlarged portion, said enlarged portion having a first part located in said second elongated hollow filter receiving handle sleeve means adjacent its open end and a second part located externally of said second elongated hollow filter receiving handle sleeve means, said first part having a seal means engaging the inner surface of said second elongated hollow filter receiving handle sleeve means, quick connect-disconnect means connecting said first part of said enlarged portion of said inner removable filter means to the end of said second elongated hollow filter receiving handle sleeve means, said second part providing means for grasping the inner removable filter means to disconnect it from said second elongated hollow filter receiving handle sleeve means to remove the inner removable filter means and reinsert it after cleaning, a tubular member extending rearwardly of said second part to collect the filtered fluid to a conventional suction tube, passage means in said enlarged portion connecting the tubular filter section to said tubular member extending from said second part of said enlarged portion.

6. A suction tip as set forth in claim 5 wherein said quick connect-disconnect means includes an annular flange on said enlarged portion of said inner removable filter means between said first and second part, said annular flange being held against the open end of said second elongated hollow filter receiving handle sleeve means when said inner removable filter means is connected to said filter receiving handle sleeve means by said connect-disconnect means.

* * * * *